United States Patent
Giori et al.

(10) Patent No.: US 6,881,426 B2
(45) Date of Patent: Apr. 19, 2005

(54) ECHINACEA ANGUSTIFOLIA EXTRACTS

(75) Inventors: Andrea Giori, Milan (IT); Alessandro Anelli, Milan (IT); Paolo Morazzoni, Milan (IT); Francesco Di Pierro, Milan (IT)

(73) Assignee: Indena S.p.A., Milan (IT)

( * ) Notice: Subject to any disclaimer, the term of this patent is extended or adjusted under 35 U.S.C. 154(b) by 44 days.

(21) Appl. No.: 10/302,842

(22) Filed: Nov. 25, 2002

(65) Prior Publication Data

US 2004/0022878 A1 Feb. 5, 2004

(30) Foreign Application Priority Data

Jul. 30, 2002 (IT) ..................................... MI2002A1691

(51) Int. Cl.[7] .............................................. A61K 35/78
(52) U.S. Cl. ........................ 424/737; 424/773; 514/233
(58) Field of Search ................................ 424/737, 773; 514/23

(56) References Cited

U.S. PATENT DOCUMENTS

| 4,857,512 A | 8/1989 | Wagner et al. |
| 5,770,217 A | 6/1998 | Kutilek, III et al. |

FOREIGN PATENT DOCUMENTS

| DE | 32 17 214 | 11/1983 |
| WO | 98/11778 | 3/1998 |
| WO | 01/22977 A2 | 4/2001 |

OTHER PUBLICATIONS

Barbara Müller–Jakic et al., "In Vitro Inhibition of Cyclooxygenase and 5–Lipoxygenase by Alkamides from *Echinacea* and *Achillea* Species," Planta Med., V. 60, 1994, pp. 37–40.
Bauer, "Echinacea containing drugs: Effects and active constituents", Zeitschrift Fur Arztliche Fortbildung 1996 Germany, vol. 90, No. 2, 1996, pp. 111–115.
Bauer et al., "TLC and HPLC Analysis of Alkamides in Echinacea Drugs" Planta Medica, vol. 55, No. 4, pp. 367–371—1989.
Bauer et al., "Echinacea preparations" Deutsche Apotheker Zeitung 1986 Germany, vol. 126, No. 20, 1986, pp. 1065–1070.
Bergeron et al., "A quantitative HPLC method for the quality assurance of Echinacea products on the North American market", Phytochemical Analysis, vol. 11, No. 4, Jul. 2000, pp. 207–215.

*Primary Examiner*—Susan D. Coe
(74) *Attorney, Agent, or Firm*—Young & Thompson

(57) ABSTRACT

An *Echinacea angustifolia* extract and a process for the preparation thereof are herein described. The extract is characterized by an alkylamides content lower than 0.1%, an echinacoside content ranging from 1 to 10% and containing from 1 to 15% of a polysaccharide characteristic of *Echinacea angustifolia*. The extract can be used for the treatment of pathological conditions in which it is desirable to strengthen the immune defenses.

16 Claims, 2 Drawing Sheets

HPLC PROFILE OF THE POLYSACCHARIDES OF THE EXTRACT OF EXAMPLE 3

HPLC PROFILE OF ECHINACOSIDE AND ALKYLAMIDES OF THE EXTRACT OF EXAMPLE 3

ECHINACEA ANGUSTIFOLIA EXTRACTS

FIELD OF THE INVENTION

The present invention relates to an extract obtainable from *Echinacea angustifolia* roots and to a process for the preparation thereof. The extract can be used in treating pathological conditions in which it is desirable to strengthen the immune defenses.

BACKGROUND OF THE INVENTION

*Echinacea* is a plant which originates from North America and Mexico; its therapeutical properties were well known to native Americans, who used it for healing wounds. Due to the fact that *Echinacea* was deemed able to increase the resistance to infections, during the first years of the last century its use for the treatment of local and generalised infections became widespread. *Echinacea*, in particular *Echinacea angustifolia*, is nowadays highly recommended for the treatment of influenza syndromes and in particular for the treatment of cold, for healing wounds and for the treatment of mycosis.

The general action is apparently due to the aspecific stimulation of the immune system and to the sensitisation of germs and pathogens to chemotherapeutics and antibiotics. The cicatrizing properties seem ascribable to the capacity of stabilizing hyaluronic acids through hyaluronidase inhibition exerted by one of the active principles contained in the plant, i.e. echinacoside, and to the massive macrophages activation induced by polysaccharides. In this way any foci of infection remain localised and accumulation of mucopolysaccharides and hystoplastic material necessary for reparative processes is favoured.

Therefore, to optimize the ability of *Echinacea* to stimulate the immune system, it would be desirable to provide extracts enriched in echinacoside and polysaccharides.

Among the active components of the plant there are also substances belonging to the class of alkylamides, in particular echinacein and isobutylamides of undecylenic and dodecaeninic acids which, besides exerting phytotherapeutic properties, inhibit cyclooxygenase (Planta Med. 60(1):37–40, 1994) and 5-lipoxygenase in vitro.

Alkylamides, although endowed with biological activity, proved highly toxic. In fact, studies carried out by the Applicant on murine splenocytes co-stimulated with concanavaline—A (Con-A) or lipopolysaccharide (LPS) in vitro, have evidenced that alkylamides are cytotoxic starting from concentrations of 1 µg/ml. Moreover, extracts containing 20% of alkylamides significantly inhibit intestinal motility in mice when administered i.p. at doses of 5 mg/ml or higher and have a $DL_{50}$ of 236 mg/Kg when administered orally. Extracts containing 0.5% of alkylamides showed also toxic in subacute toxicity experiments, i.e. when the animals were treated for 30 days with pharmacologically active doses.

It would be therefore desirable to prepare *Echinacea* extracts with reduced alkylamides content and enriched in echinacoside and polysaccharides.

*Echinacea* extracts can be prepared with solvents, for example with ethanol-water mixtures or with supercritical carbon dioxide.

WO 01/22977 discloses a process for the preparation of *Echinacea* extracts containing standardized amounts of two or three components of the plant, in particular polysaccharides, cicoric acid and alkylamides. Each component is extracted from different parts of the plant with ethanol-water mixtures, for prolonged times. The extracts are subsequently combined for the preparation of pharmaceutical compositions.

DETAILED DISCLOSURE OF THE INVENTION

Figure 1:
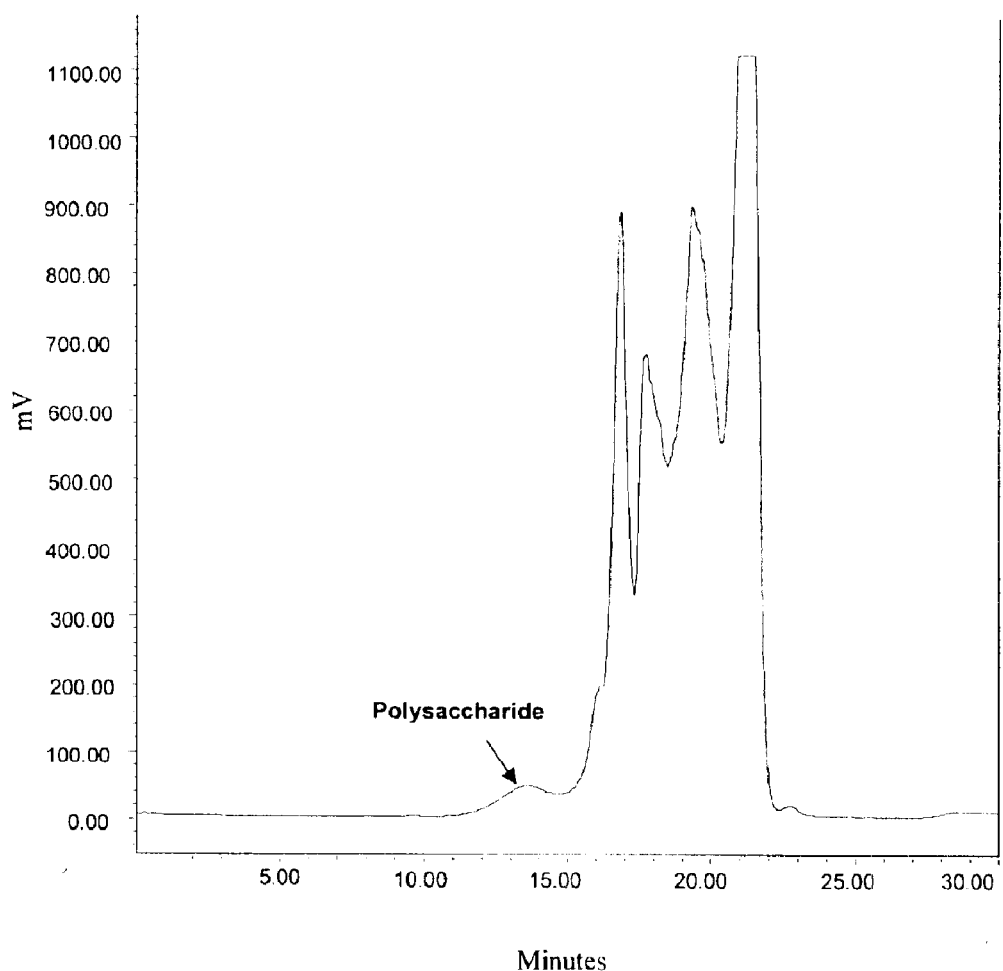
FIG. 1 shows the HPLC of the polysaccharides of the extract of Example 3.
Figure 2:
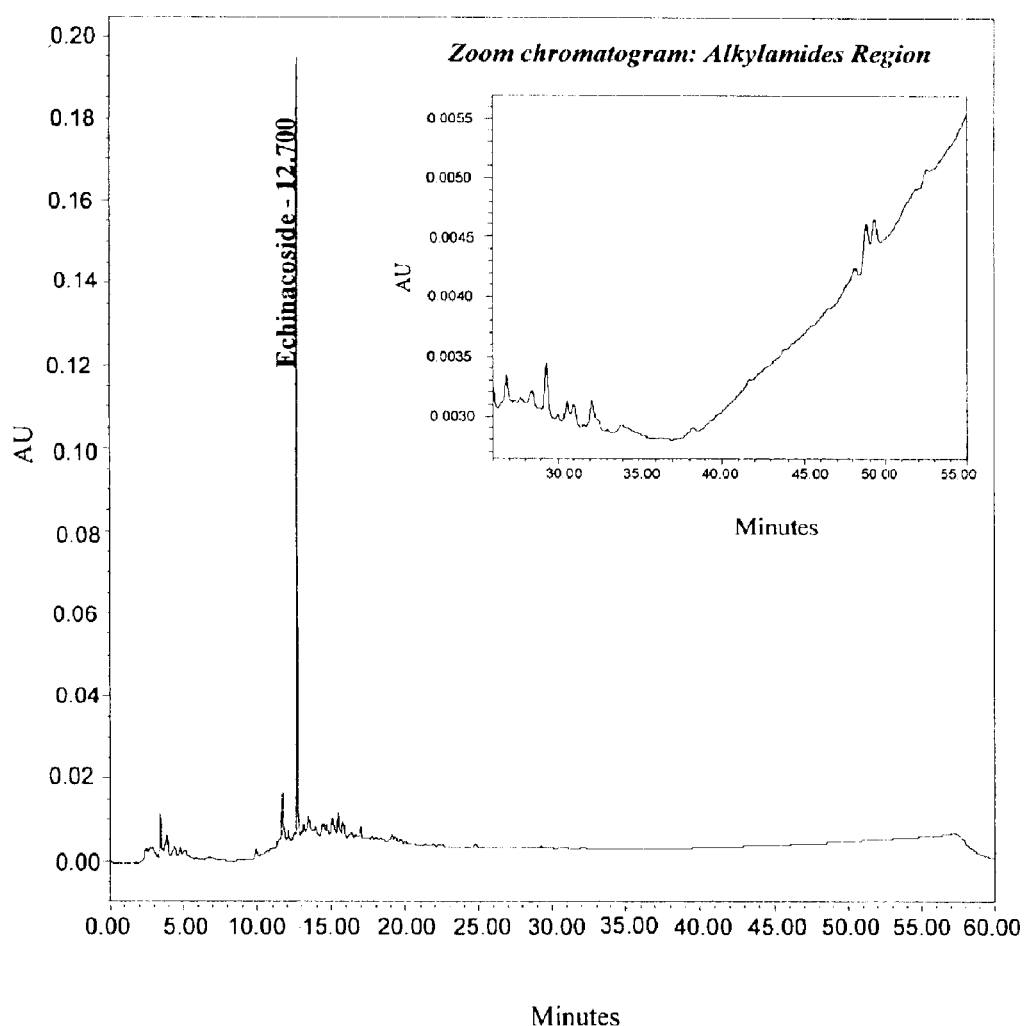
FIG. 2 shows the HPLC profile of echinacoside and alkylamides of the extract of Example 3.

Object of the present invention is an extract of *Echinacea angustifolia* characterized by an alkylamides content lower than 0.1%, an echinacoside content ranging from 1 to 10% and containing from 1 to 15% of a polysaccharide characteristic of *Echinacea angustifolia* (hereinafter referred to as "the polysaccharide"). The polysaccharide weighs $1.3 \times 10^5$ Da and consists of rhamnose, arabinose, galactose and galacturonic acid in 0.5:2.5:1.75:10.25 ratio, has a skeleton wherein straight and branched portions alternate, the straight portions consisting of partially acetylated (9%) and methylated (35%) galacturonic acid residues linked via α-(1-4) bond and the branched portions consisting of an alternation of galacturonic acid and rhamnose, to which side chains containing arabinose and galactose in 2.5:1.75 ratio are attached.

The extract is prepared from the roots of spontaneous or cultivated *Echinacea angustifolia*, by means of a process comprising the following steps:

1. extracting the roots with an organic solvent or with an organic solvent-water mixture having a water content not higher than 40% (v/v) and repeatedly washing the pooled and concentrated extracts with an apolar solvent;
2. extracting the roots with water or with an organic solvent-water mixture having a water content of 60% (v/v) or higher, preferably from 80 to 85% (v/v);
3. mixing the extracts obtained in the preceding steps.

For the purposes of the present invention, "organic solvent" means an organic solvent selected from acetone or an alcohol containing one to three carbon atoms, preferably ethanol.

The first step, which allows to remove the alkylamide components and to obtain an extract enriched in Echinacoside, preferably comprises:

1a. extracting the roots at temperature ranging from 20° C. to the reflux temperature of the organic solvent or of the water-organic solvent mixture, preferably under reflux;
1b. concentrating the combined extracts to small volume;
1c. dissolving the concentrate in a water-organic solvent mixture having a water content not lower than 50%;
1d. repeatedly washing the water-organic solvent mixture with an apolar solvent, selected for example from petroleum ether, pentane, hexane or heptane, preferably hexane;
1e. evaporating the water-organic solvent mixture.

The second step, which allows to obtain an extract enriched in polysaccharide, preferably comprises:

2a. extracting the roots from the extraction step at a temperature ranging from 20° C. to the boiling temperature of water or of the solvent mixture, preferably from 40 to 70° C.;
2b. concentrating the extract to small volume;
2c. dissolving the residue in a water-organic solvent mixture, the organic solvent content ranging from 50 to 70% (v/v), to obtain a precipitate;

2d. filtering and washing the precipitate with the same solvent mixture.

According to a preferred embodiment of the invention, step 2c is carried out with ethanol, more preferably with 66.5% (v/v) ethanol, i.e. dissolving the residue obtained in step 2b in three parts of water and diluting with 7 volumes of 95% ethanol (v/v), at room temperature and under stirring.

The third step preferably comprises:

3a. dissolving the pooled extracts from the preceding steps in a water-organic solvent mixture, the preferred organic solvent being ethanol having a water content of 60% (v/v) or higher, preferably ranging from 80 to 85% (v/v);

3b. concentrating the water-organic solvent solution and drying under reduced pressure.

The extraction of step 1a is preferably carried out with 90% (v/v) ethanol, whereas the extraction of step 2a is preferably carried out with 15% (v/v) ethanol.

The extract of the invention showed immune-stimulating properties in mice, in particular proved able to stimulate T-lymphocytes activation and to reduce the mortality due to *Candida albicans* infection in mice immuno-suppressed with cyclosporin A. The extract of the invention can be therefore used for the preparation of medicaments, food supplements or nutraceutical compositions to administer in conditions in which an increase of the immune system body defenses is desirable.

The extract can be formulated according to conventional techniques, for example according to those described in Remington's Pharmaceutical Sciences Handbook, XVII ed. Mack Pub., N.Y., U.S.A.

The present invention is hereinafter illustrated by means of some examples.

EXAMPLES

Example 1

Step 1: Preparation of the Echinacoside-Enriched Extract 600 grams of ground roots of *Echinacea angustifolia* are placed in a percolator and extracted under reflux for four hours with 2.5 L of 90% (v/v) ethanol. After collecting the percolate, seven further extractions are carried out with the same solvent; the percolates are pooled and the roots are preserved for the following step.

The combined percolates are filtered and concentrated to small volume under reduced pressure. The concentrate is diluted with water and ethanol to give a 50% (v/v) ethanol solution, which is then extracted ten times with hexane. The hexane layers, which contain alkylamides, are discarded.

The purified hydroethanolic solution is concentrated to dryness under reduced pressure, to afford 78.5 g of extract (echinacoside HPLC titre: 9.8%; alkylamides HPLC titre: 0.07%).

Example 2

Step 2: Preparation of the Polysaccharide-Enriched Extract

The *Echinacea angustifolia* roots obtained from the extraction with 90% (v/v) ethanol according to example 1 are further extracted eight times with 2.5 L of 15% (v/v) ethanol at 70° C.

The combined percolates are filtered and concentrated to dryness under reduced pressure. The resulting dry extract (171 g) is dissolved in 510 ml of water, and 1200 ml of 95% (v/v) ethanol are added under stirring. The precipitate is filtered, washed with 66.5% (v/v) ethanol and dried at 60° C. under reduced pressure, to afford 130 g of purified extract (polysaccharide GPC titre: 8.9%).

Example 3

Mixing the Intermediate Extracts 78.5 g of the echinacoside-enriched extract are combined with 106.5 g of the polysaccharide-enriched extract. The mixture is taken up with 925 ml of 15% (v/v) ethanol, stirred for 1 hour and concentrated to dryness under reduced pressure, to afford 185 g of *Echinacea angustifolia* extract (echinacoside HPLC titre: 4.2%; alkylamides HPLC titre: 0.04%; polysaccharide HPLC titre 5.12%).

The HPLC profile of the extract is reported in FIGS. 1 (non-polysaccharide fraction) and 2 (polysaccharide fraction).

Example 4

HPLC Determination of the Polysaccharide Content

The characterization of the extracts that contain the polysaccharide of the invention is carried out with a Toso-Haas TSK-Gel G 5000 PWXL column eluted with water containing 0.5% of triethylamine in isocratic conditions at a flow rate of 0.5 ml/min. During the analysis, which lasts 30 minutes, the column is kept at 50° C.

The injection volume is 50 μl. An evaporative detector ELSD (Evaporative Light Scattering Detector) Sedex mod. 75 (S. E. D. E. R. E.)—whose nebulizer is kept at 60° C. with gas pressure of 2.2 bars is coupled to the column.

Example 5

HPLC Determination of the Echinacoside and Alkylamides Content

The HPLC determination of the echinacoside and alkylamides content in *Echinacea angustifolia* extracts is carried out with an Agilent Zorbax SB-C18 reverse-phase column coupled to a UV-visibile detector (wavelength 235 nm), eluted with a suitable water/acetonitrile gradient containing 0.01% of trifluoroacetic acid at a flow rate of 1.0 ml/min. During the analysis, which lasts 60 minutes, the column is kept at room temperature.

The injection volume is 10 μl.

Biological Section

Experiment 1

Test for the Production of γ-Interferon in T-lymphocytes (Zucca M. et al, New Microbiol. 1996, 19, 39–46)

Murine T-lymphocytes obtained by separation of splenocytes on nylon-wool column were cultured in 1640 RPMI medium with 4% of fetal calf serum in microtitre plates optionally pre-incubated with α-CD3 (anti-CD3 monoclonal antibody as cell function activator responsible for interferon production). 48 Hours after the addition of the substances to test, the release of γ-interferon in the incubation medium was evaluated.

TABLE 1

| TREATMENT | γ-Interferon pg/ml |
|---|---|
| Medium | 4.5 ± 0.5 |
| α-CD3 | 149.5 ± 25.0 |
| α-CD3 + extract of example 5, 0.1 μg/ml | 280.0 ± 35.8 |
| α-CD3 + extract of example 5, 1.0 μg/ml | 355.8 ± 61.4 |
| α-CD3 + extract of example 5, 10.0 μg/ml | 442.0 ± 70.5 |

Experiment 2

Effect on Mortality Induced by *Candida albicans* in Mice (Microbiology 2000, 146,1881–9)

Yeasts were cultivated over Sabouraud agarized medium and inoculated intravenously at a concentration of $3.5 \times 10^5$ in non-immunosuppressed mice and at a concentration of $2.9 \times 10^5$ in mice immune-suppressed with 1 mg/Kg i.p. of cyclosporin A (CsA). Mice were treated daily i.p. with 5 and 10 mg/Kg of the extract of the invention until death of all the control mice (untreated). The results were evaluated as survived animals in the treated groups.

TABLE 2

| TREATMENT | % OF SURVIVED ANIMALS |
|---|---|
| *Candida albicans* (CA) + CsA | 0 |
| CA + extract of example 5, 500 mg/kg | 20 |
| CA + extract of example 5, 1000 mg/kg | 40 |
| CA + Csa | 0 |
| CA + CsA + extract of example 5, 500 mg/kg | 30 |
| CA + CsA + extract of example 5, 1000 mg/kg | 60 |

What is claimed is:

1. An *Echinacea angustifolia* extract characterized by an alkylamides content lower than 0.1%, an echinacoside content ranging from 1 to 10% and a polysaccharide content ranging from 1 to 15%, the polysaccharide weighing $1.3 \times 10^5$ Da and consisting of rhamnose, arabinose, galactose and galacturonic acid in 0.5:2.5:1.75:10.25 ratio.

2. The extract according to claim 1 wherein the polysaccharide has a skeleton with alternate straight and branched portions, the straight portions consisting of partially acetylated and methylated galacturonic acid residues linked via α-(1-4) bond and the branched portions consisting of an alternation of galacturonic acid and rhamnose, to which side chains containing arabinose and galactose in 2.5:1.75 ratio are attached.

3. A process for the preparation of the extract according to claim 1 comprising the following steps:
   extracting roots with an organic solvent or with an organic solvent-water mixture having a water content not higher than 40% (v/v) and subsequently washing pooled and concentrated extracts with an apolar solvent;
   further extracting said roots with water or with an organic solvent-water mixture having a water content of 60% (v/v) or higher;
   mixing the extracts obtained in the preceding steps.

4. The process according to claim 3 wherein the organic solvent is selected from acetone or an alcohol having 1 to 3 carbon atoms.

5. The process according to claim 3 wherein the organic solvent is ethanol.

6. The process according to claim 3 wherein said step of extracting the roots with an organic solvent or with an organic solvent-water mixture having a water content not higher than 40% (v/v) and subsequently washing pooled and concentrated extracts with an apolar solvent, comprises:
   a. extracting the roots at a temperature ranging from 20° C. to the reflux temperature of the organic solvent or of the water-organic solvent mixture;
   b. concentrating said pooled extracts to obtain a concentrate;
   c. dissolving said concentrate in a water-organic solvent mixture having a water content not lower than 50% (v/v);
   d. repeatedly washing the water-organic solvent mixture with an apolar solvent;
   e. evaporating the water-organic solvent mixture.

7. The process according to claim 6 wherein the organic solvent independently used in steps a and c is selected from acetone and an alcohol having 1 to 3 carbon atoms.

8. The process according to claim 6 wherein the apolar solvent of step d is selected from petroleum ether, pentane, hexane or heptane.

9. The process according to claim 8 wherein the solvent is hexane.

10. The process according to claim 3 wherein said step of further extracting said roots with water or with an organic solvent-water mixture having a water content of 60% (v/v) or higher, comprises:
    extracting said roots at a temperature ranging from 20° C. to the boiling temperature of water or of the solvent mixture;
    concentrating the extract;
    dissolving the concentrated extract in a water-organic solvent mixture having an organic solvent content ranging from 50 to 70%, to obtain a precipitate;
    filtrating and washing the precipitate with the same solvent mixture.

11. The process according to claim 10 wherein the organic solvent is selected from acetone and an alcohol having 1 to 3 carbon atoms.

12. The process according to claim 3 wherein said step of mixing the extracts obtained in the preceding steps, comprises:
    dissolving the combined extracts obtained in the preceding steps in a water-organic solvent mixture, with a water content of 60% (v/v) or higher to obtain a water-alcohol solution;
    concentrating the water-alcohol solution and drying under reduced pressure.

13. The process according to claim 12 wherein the organic solvent is acetone or an alcohol having 1 to 3 carbon atoms.

14. The process according to claim 13 wherein the alcohol is ethanol.

15. A pharmaceutical or nutraceutical composition or food supplement containing the extract of claim 1 in admixture with suitable excipients and, or carriers.

16. A method for stimulating the immune system in a patient, comprising:
    administering an effective amount of the extract according to claim 1 to said patient.

* * * * *